US010457634B2

(12) United States Patent
Erlandsson et al.

(10) Patent No.: US 10,457,634 B2
(45) Date of Patent: *Oct. 29, 2019

(54) PROCESS FOR THE PRODUCTION OF FORMALDEHYDE

(71) Applicant: JOHNSON MATTHEY PUBLIC LIMITED COMPANY, London (GB)

(72) Inventors: Ola Erlandsson, Höör (SE); Andreas Magnusson, Lund (SE); John David Pach, Cleveland (GB); Daniel Sheldon, Cleveland (GB)

(73) Assignee: Johnson Matthey Public Limited Company, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 16/113,859

(22) Filed: Aug. 27, 2018

(65) Prior Publication Data

US 2018/0362453 A1    Dec. 20, 2018

Related U.S. Application Data

(62) Division of application No. 15/552,072, filed as application No. PCT/GB2015/054082 on Dec. 18, 2015, now Pat. No. 10,087,140.

(30) Foreign Application Priority Data

Feb. 20, 2015   (GB) .................................. 1502894.7

(51) Int. Cl.
C07C 273/14     (2006.01)
C07C 29/151     (2006.01)
(Continued)

(52) U.S. Cl.
CPC ............ C07C 273/14 (2013.01); C01B 3/025 (2013.01); C01B 3/382 (2013.01); C01B 3/48 (2013.01);
(Continued)

(58) Field of Classification Search
None
See application file for complete search history.

(56) References Cited

U.S. PATENT DOCUMENTS 3,598,527 A    8/1971  Quartulli et al.
4,072,717 A    2/1978  Halbritter et al.
(Continued)

FOREIGN PATENT DOCUMENTS

EP    2805914 A1    11/2014
FR    2903688    *    1/2008
(Continued)

OTHER PUBLICATIONS

Reimert, "Gas Production, 2.Processes" Ullmann's Encyclopedia of Industrial Chemistry, 2011, p. 423-482, downloaded from https://onlinelibrary.wiley.com/doi/full/10.1002/14356007.o12_o01 on Feb. 28, 2019) (Year: 2011).*

(Continued)

Primary Examiner — Amy C Bonaparte
(74) Attorney, Agent, or Firm — BakerHostetler

(57) ABSTRACT

A process is described for the production of formaldehyde, comprising (a) subjecting methanol to oxidation with air in a formaldehyde production unit thereby producing a formaldehyde-containing stream; (b) separating said formaldehyde-containing stream into a formaldehyde product stream and a formaldehyde vent gas stream; wherein the vent gas stream, optionally after treatment in a vent gas treatment unit, is passed to one or more stages of: (i) synthesis gas generation, (ii) carbon dioxide removal, (iii) methanol synthesis or (iv) urea synthesis.

10 Claims, 2 Drawing Sheets

(51) Int. Cl.

| | |
|---|---|
| *C07C 273/04* | (2006.01) |
| *C07C 45/38* | (2006.01) |
| *C01B 3/38* | (2006.01) |
| *C01C 1/04* | (2006.01) |
| *C01B 3/02* | (2006.01) |
| *C01B 3/48* | (2006.01) |
| *C01B 3/52* | (2006.01) |
| *C01B 3/56* | (2006.01) |
| *C07C 45/29* | (2006.01) |
| *C07C 273/10* | (2006.01) |
| *C10J 3/82* | (2006.01) |

(52) U.S. Cl.
CPC .............. *C01B 3/52* (2013.01); *C01B 3/56* (2013.01); *C01C 1/0488* (2013.01); *C07C 29/1518* (2013.01); *C07C 45/29* (2013.01); *C07C 45/38* (2013.01); *C07C 273/04* (2013.01); *C07C 273/10* (2013.01); *C10J 3/82* (2013.01); *C01B 2203/025* (2013.01); *C01B 2203/0233* (2013.01); *C01B 2203/0244* (2013.01); *C01B 2203/0283* (2013.01); *C01B 2203/042* (2013.01); *C01B 2203/043* (2013.01); *C01B 2203/0415* (2013.01); *C01B 2203/0475* (2013.01); *C01B 2203/061* (2013.01); *C01B 2203/062* (2013.01); *C01B 2203/068* (2013.01); *C01B 2203/1241* (2013.01); *C01B 2203/1252* (2013.01); *C01B 2203/141* (2013.01); *C01B 2203/142* (2013.01); *C01B 2203/145* (2013.01); *C01B 2203/148* (2013.01); *C10J 2300/093* (2013.01); *C10J 2300/0916* (2013.01); *C10J 2300/0956* (2013.01); *C10J 2300/0959* (2013.01); *C10J 2300/0976* (2013.01); *C10J 2300/1838* (2013.01); *C10J 2300/1853* (2013.01); *Y02E 50/18* (2013.01); *Y02P 20/52* (2015.11)

(56) References Cited

U.S. PATENT DOCUMENTS

| | | | | |
|---|---|---|---|---|
| 4,383,123 A * | 5/1983 | Ferris | ............... | C07C 45/38 |
| | | | | 568/473 |
| 4,454,354 A * | 6/1984 | Ferris | ............... | C07C 29/80 |
| | | | | 568/472 |
| 5,173,513 A | 12/1992 | Pinto | | |
| 5,965,071 A | 10/1999 | Hidetsugu et al. | | |
| 6,106,793 A | 8/2000 | Badano et al. | | |
| 6,333,014 B1 | 12/2001 | Filippi | | |
| 7,521,483 B2 | 4/2009 | Davey et al. | | |
| 8,247,463 B2 * | 8/2012 | Yoshida | ............... | B01J 8/0411 |
| | | | | 252/373 |
| 8,303,923 B2 * | 11/2012 | Han | ............... | C01B 3/382 |
| | | | | 423/359 |
| 10,077,235 B2 * | 9/2018 | Erlandsson | ............ | C01B 3/025 |
| 10,087,140 B2 * | 10/2018 | Erlandsson | ........ | C07C 29/1518 |
| 2002/0035291 A1 | 3/2002 | Melnichuk et al. | | |
| 2007/0299144 A1 * | 12/2007 | Davey | ............... | C01B 3/025 |
| | | | | 518/703 |
| 2019/0031604 A1 * | 1/2019 | Erlandsson | ............ | C07C 45/29 |

FOREIGN PATENT DOCUMENTS

| | | | |
|---|---|---|---|
| FR | 2903688 A1 | | 1/2008 |
| GB | 1057327 | * | 2/1967 |
| GB | 1245593 A | | 9/1971 |
| GB | 1339926 A | | 12/1973 |
| GB | 1536011 A | | 12/1978 |
| WO | WO 2004096758 A1 | | 11/2004 |
| WO | WO 2013102589 A1 | | 7/2013 |

OTHER PUBLICATIONS

"Boosting Profitability for Urea Producers," 6th GPCA Fertilizer Convention Integration of Urea-Formaldehyde Production, Sep. 16, 2015, pp. 1-18 [cited in parent U.S. Appl. No. 15/552,072].

Shields, V.L. et al., "Coproduction of Ammonia and Methanol," from AIChE; Ammonia Safety Committee Annual Symposium, 40th Ammonia Plant Safety and Related Facilities; 1995; Tuscon, AZ, published in Ammonia Plant Safety and Related Facilities, 36, pp. 259-267, 1996 [cited in parent U.S. Appl. No. 15/552,072].

Soegaard-Andersen, P. et al., "Methanolation in Ammonia Plants," from AIChE; Ammonia Safety Committee Safety Symposium, Ammonia Plant Safety and Related Facilities; 1991, Los Angeles, CA, 32, pp. 177-186, 1992 [cited in parent U.S. Appl. No. 15/552,072].

GB 1502894.7, UK Search Report under Section 17(5) dated Dec. 11, 2015.

GB1522403.3 UK Examination Report under Section 18(3) dated Apr. 7, 2017.

PCT/GB2015/054082, International Search Report dated Mar. 4, 2016.

PCT/GB2015/054082, Written Opinion dated Mar. 4, 2016.

PCT/GB2015/054082, International Preliminary Report on Patentability dated Aug. 22, 2017.

* cited by examiner

PROCESS FOR THE PRODUCTION OF FORMALDEHYDE

CROSS-REFERENCE TO RELATED APPLICATIONS

This application is a divisional of U.S. patent application Ser. No. 15/552,072, filed Aug. 18, 2017, which is a national stage application of International Patent Application No. PCT/GB2015/054082, filed Dec. 18, 2015, which claims the benefit of priority of Great Britain Patent Application No. 1502894.7, filed Feb. 20, 2015, the disclosures of which are hereby incorporated by reference in their entireties.

FIELD OF THE INVENTION

The present invention relates to a process for the production of formaldehyde. More particularly, it relates to a process for the production of formaldehyde which may be integrated into a flow-sheet for the production of formaldehyde-containing products, such as, for example, formaldehyde-stabilised urea in a process including the co-production of methanol and ammonia.

BACKGROUND

Urea finds widespread use as a fertiliser and in industrial chemical manufacture. It is conventionally made by reacting ammonia with carbon dioxide to form a solid product which is often shaped by prilling or granulating. Formaldehyde or a urea-formaldehyde concentrate (UFC) are often used to stabilise the urea before or during the shaping process. UFC is also used as a feedstock for the manufacture of urea-formaldehyde resins.

Formaldehyde is manufactured by the oxidation or dehydrogenation of methanol. There is scope for providing an integrated process in which the production of formaldehyde is integrated with a flowsheet involving the production of one or more formaldehyde-containing precursors or products, leading to more efficient use of energy and/or of feedstocks.

However, the demand for formaldehyde to stabilise the urea from a single production facility is small and beyond the economic feasibility for a dedicated formaldehyde production facility. Due to the small scale of the requirements, the formaldehyde is normally produced at a separate dedicated formaldehyde production facility and transported to the ammonia/urea production facility where it is stored. An integrated urea-formaldehyde process with a dedicated formaldehyde production unit based on a methanol-ammonia co-production process which improves the ammonia productivity and does not reduce urea production therefore has the potential to provide efficiency savings compared with a conventional process

SUMMARY

Accordingly the invention provides a process for the production of formaldehyde, comprising (a) subjecting methanol to oxidation with air in a formaldehyde production unit thereby producing a formaldehyde-containing stream; (b) separating said formaldehyde-containing stream into a formaldehyde product stream and a formaldehyde vent gas stream; wherein the vent gas stream, optionally after treatment in a vent gas treatment unit, is passed to one or more stages of: (i) synthesis gas generation, (ii) carbon dioxide removal, (iii) methanol synthesis or (iv) urea synthesis.

BRIEF DESCRIPTION OF THE DRAWINGS

The present invention will now be described by way of example with reference to the accompanying drawings in which.

Figure 1:
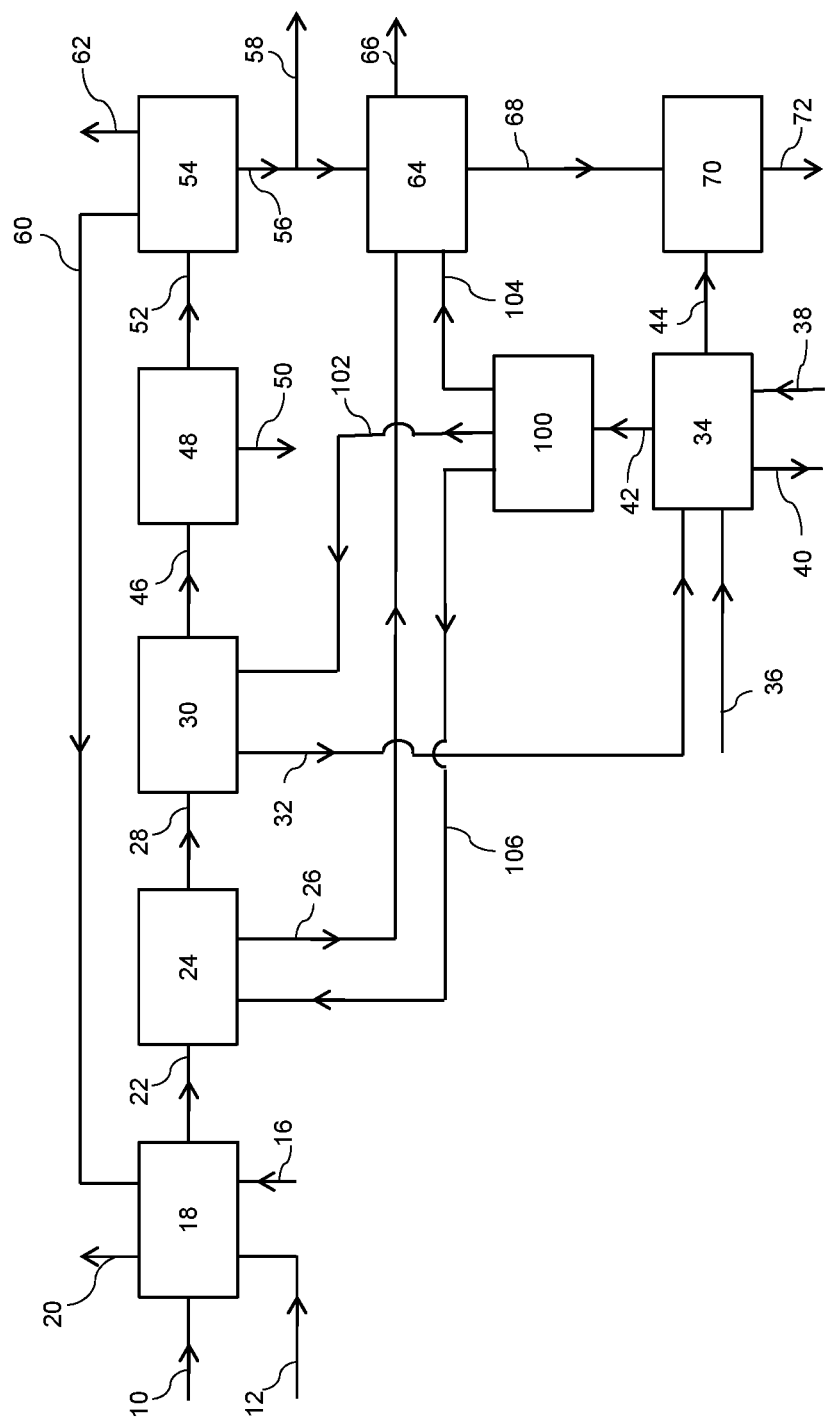
FIG. 1 is a schematic representation of a process according to a first aspect of the present invention.

It will be understood by those skilled in the art that the drawings are diagrammatic and that further items of equipment such as reflux drums, pumps, vacuum pumps, temperature sensors, pressure sensors, pressure relief valves, control valves, flow controllers, level controllers, holding tanks, storage tanks, and the like may be required in a commercial plant. The provision of such ancillary items of equipment forms no part of the present invention and is in accordance with conventional chemical engineering practice.

DETAILED DESCRIPTION

In one embodiment, the invention provides a process for the production of formaldehyde-stabilised urea, comprising (a) subjecting methanol to oxidation with air in a formaldehyde production unit thereby producing a formaldehyde-containing stream; (b) separating said formaldehyde-containing stream into a formaldehyde product stream and a formaldehyde vent gas stream; (c) synthesising urea in a urea production unit; and (d) stabilising the urea by mixing the urea and a stabiliser prepared using formaldehyde recovered from said formaldehyde product stream, wherein the formaldehyde vent gas stream, optionally after treatment in a vent gas treatment unit, is passed to one or more stages of: (i) synthesis gas generation, (ii) carbon dioxide removal, (iii) methanol synthesis or (iv) urea synthesis employed in the production of urea or formaldehyde.

There have been numerous designs for ammonia and methanol co-production over the last 50 years or so, but they have generally focussed on generating large quantities of both materials as saleable products. Examples of such processes are described, for example in U.S. Pat. Nos. 6,106,793, 6,333,014, 7,521,483, 8,247,463, 8,303,923, and WO2013/102589. None of these processes include a dedicated formaldehyde production unit with vent gas recycle as claimed. As the present invention utilises recycle of the vent gas from the formaldehyde production unit, substantial benefits in the reduction of capital and operating costs are possible, in particular where the vent gas stream is recycled directly to the process.

In a conventional formaldehyde production process, the formaldehyde production unit comprises a formaldehyde reactor, in which methanol is oxidised to produce formaldehyde, and a separation unit in which the formaldehyde product is separated from the formaldehyde vent gas. The formaldehyde vent gas separated from the formaldehyde product stream may contain nitrogen, oxygen, carbon monoxide, water and organics including methanol, formaldehyde and dimethyl ether. In a typical formaldehyde production process, the formaldehyde vent gas stream may be recirculated to the formaldehyde reactor and a portion vented to the atmosphere, usually after treatment in a vent gas treatment unit such as an emissions control system (ECS). The ECS may comprise non-selective oxidation of the organic compounds in the formaldehyde vent gas stream in order to remove them from the gas prior to atmospheric venting. It is usually necessary to treat at least some of the formaldehyde vent gas in this way because the recirculated gas contains methanol and the admixture with air needs to avoid the risk of explosion; therefore it is not possible to recirculate all of the vent gas to the formaldehyde reactor. The ECS represents a major capital cost in the building of a formaldehyde plant and requires operation and maintenance, thereby adding to the cost of the formaldehyde production unit. Advantageously, in the process of the invention, the formaldehyde vent gas need not be treated in an ECS.

The process may comprise a synthesis gas generation step in a synthesis gas generation unit, and conversion of the synthesis gas to methanol for use in step (a) of the process. The synthesis gas may also be used to produce ammonia, in particular for the production of urea using carbon dioxide recovered from the synthesis gas.

The synthesis gas preferably comprises hydrogen, nitrogen, carbon monoxide, carbon dioxide and steam. The synthesis gas may be generated by any suitable means. The synthesis gas generation may be based on steam reforming of a hydrocarbon such as natural gas, naphtha or a refinery off-gas; or by the gasification of a carbonaceous feedstock, such as coal or biomass. Preferably the synthesis gas generation stage comprises steam reforming a hydrocarbon. This may be achieved by primary reforming a hydrocarbon with steam in externally-heated catalyst-filled tubes in a fired- or gas-heated steam reformer and, where the methane content of the primary reformed gas is high, secondary reforming the primary-reformed gas mixture in a secondary reformer, by subjecting it to partial combustion with an oxygen-containing gas and then passing the partially combusted gas mixture through a bed of steam reforming catalyst. The oxygen-containing gas may be air, oxygen or oxygen-enriched air. The formaldehyde vent gas stream from the formaldehyde production unit may be used in the synthesis gas generation unit as a feedstock or alternatively as a fuel for heating a reformer unit.

Whereas secondary reforming with air or oxygen-enriched air usefully provides the nitrogen in the reaction stream, the synthesis gas may be produced by primary steam reforming or autothermally reforming a hydrocarbon feed using oxygen alone and providing nitrogen from another source, such as an air separation unit (ASU).

The primary reforming catalyst typically comprises nickel at levels in the range 5-30% wt, supported on shaped refractory oxides, such as alpha alumina, magnesium aluminate or calcium aluminate. If desired, catalysts with different nickel contents may be used in different parts of the tubes, for example catalysts with nickel contents in the range 5-15% wt or 30-85% wt may be used advantageously at inlet or exit portions of the tubes. Alternatively, structured catalysts, wherein a nickel or precious metal catalyst is provided as a coated layer on a formed metal or ceramic structure may be used, or the catalysts may be provided in a plurality of containers disposed within the tubes. Steam reforming reactions take place in the tubes over the steam reforming catalyst at temperatures above 350° C. and typically the process fluid exiting the tubes is at a temperature in the range 650-950° C. The heat exchange medium flowing around the outside of the tubes may have a temperature in the range 900-1300° C. The pressure may be in the range 10-80 bar abs. In a secondary reformer, the primary-reformed gas is partially combusted in a burner apparatus mounted usually near the top of the reformer. The partially combusted reformed gas is then passed adiabatically through a bed of steam reforming catalyst disposed below the burner apparatus, to bring the gas composition towards equilibrium. Heat for the endothermic steam reforming reaction is supplied by the hot, partially combusted reformed gas. As the partially combusted reformed gas contacts the steam reforming catalyst it is cooled by the endothermic steam reforming reaction to temperatures in the range 900-1100° C. The bed of steam reforming catalyst in the secondary reformer typically comprises nickel at levels in the range 5-30% wt, supported on shaped refractory oxides, but layered beds may be used wherein the uppermost catalyst layer comprises a precious metal, such as platinum or rhodium, on a zirconia support. Such steam reforming apparatus and catalysts are commercially available.

Alternatively, the steam reforming maybe achieved by passing a mixture of the hydrocarbon and steam through an adiabatic pre-reformer containing a bed of steam reforming catalyst and then passing the pre-reformed gas mixture to an autothermal reformer which operates in the same way as the secondary reformer to produce a gas stream containing hydrogen, carbon oxides and steam. In adiabatic pre-reforming, a mixture of hydrocarbon and steam, typically at a steam to carbon ratio in the range 1-4, is passed at an inlet temperature in the range 300-620° C. to a fixed bed of pelleted nickel-containing pre-reforming catalyst. Such catalysts typically comprise ≥40% wt nickel (expressed as NiO) and may be prepared by co-precipitation of a nickel-containing material with alumina and promoter compounds such as silica and magnesia. Again, the pressure may be in the range 10-80 bar abs.

Alternatively, the reaction stream may be formed by gasification of coal, biomass or other carbonaceous material with air using gasification apparatus. In such processes the coal, biomass or other carbonaceous material is heated to high temperatures in the absence of a catalyst to form a crude synthesis gas often containing sulphur contaminants such as hydrogen sulphide, which have to be removed. Gasification of carbonaceous feedstock to produce a synthesis gas may be achieved using known fixed bed, fluidised-bed or entrained-flow gasifiers at temperatures in the range 900-1700° C. and pressures up to 90 bar abs. The crude synthesis gas streams require additional treatments known in the art to remove unwanted sulphur and other contaminants.

In a preferred process, the synthesis gas generation stage comprises primary reforming a hydrocarbon, particularly natural gas, in a fired steam reformer to produce a gas stream comprising hydrogen, carbon monoxide, carbon dioxide and steam, and secondary reforming stage in which the primary reformed gas is further reformed in a secondary reformer using air or oxygen-enriched air to provide a synthesis gas stream comprising hydrogen, carbon oxides and nitrogen.

The process may include a stage of removing carbon dioxide from the synthesis gas. Before recovery of the carbon dioxide, the crude synthesis gas is preferably subjected to one or more stages of water-gas shift to produce a shifted synthesis gas with the desired gas composition. In a water gas shift stage, a portion of the carbon monoxide in the stream is converted to carbon dioxide. Any suitable catalytic shift conversion reactor and catalyst may be used. If insufficient steam is present, steam may be added to the gas stream before it is subjected to the water-gas shift conversion. The reaction may be depicted as follows;

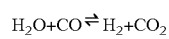

The vent gas from the formaldehyde production unit typically contains steam and CO which may be used in the feed to the water-gas shift reaction. The reaction may be carried out in one or more stages. The, or each, stage may be the same or different and may be selected from a high temperature shift process, a low temperature shift process, a medium temperature shift process and an isothermal shift process.

High temperature shift catalysts may be promoted iron catalysts such as chromia- or alumina-promoted magnetite catalysts. Other high temperature shift catalysts may be used, for example iron/copper/zinc oxide/alumina catalysts, manganese/zinc oxide catalysts or zinc oxide/alumina catalysts. Medium, low temperature and isothermal shift catalysts typically comprise copper, and useful catalysts may comprise varying amounts of copper, zinc oxide and alumina. Alternatively, where sulphur compounds are present in the gas mixture, such as synthesis gas streams obtained by gasification, so-called sour shift catalysts, such as those comprising sulphides of molybdenum and cobalt, are preferred. Such water-gas shift apparatus and catalysts are commercially available.

For high temperature shift catalysts, the temperature in the shift converter may be in the range 300-360° C., for medium temperature shift catalysts the temperature may be in the range 190-300° C. and for low-temperature shift catalysts the temperature may be 185-270° C. For sour shift catalysts the temperature may be in the range 200-370° C. The flow-rate of synthesis gas containing steam may be such that the gas hourly space velocity (GHSV) through the bed of water-gas shift catalyst in the reactor may be ≥6000 hour$^{-1}$. The pressure may be in the range 10-80 bar abs.

In a preferred embodiment, the water-gas shift stage comprises a high temperature shift stage or a medium temperature shift stage or an isothermal shift stage with or without a low temperature shift stage.

Steam present in the shifted synthesis gas mixture may be condensed by cooling the shifted gas to below the dew point using one or more heat exchangers fed, for example, with cooling water. The condensate may be recovered in a gas liquid separator and may be fed to steam generators that produce steam for the synthesis gas or water-gas shift stages.

A carbon dioxide removal unit may be used to recover carbon dioxide from the synthesis gas. If present, it is located downstream of the synthesis gas generation, preferably downstream of a water-gas shift stage, and upstream of a methanol synthesis unit. Any suitable carbon dioxide removal unit may be used. Suitable removal units may function by reactive absorption, such as those known as aMDEA™ or Benfield™ units that are based on using regenerable amine or potassium carbonate washes, or by physical absorption, based on using methanol, glycol or another liquid at low temperature, such as Rectisol™, Selexol™ units. Carbon dioxide removal may also be performed by means of pressure-swing adsorption (PSA) using suitable solid adsorbent materials. The carbon dioxide removal unit, if operated using physical absorption at low temperature, is able to simultaneously remove residual steam in the shifted synthesis gas by condensation. Such carbon dioxide removal apparatus and materials are commercially available. Some or all of the carbon dioxide formed in the synthesis gas may be removed to produce a gas stream comprising mainly hydrogen and nitrogen with low levels of carbon monoxide. The carbon dioxide removed by the carbon dioxide removal unit may be captured, treated to remove contaminants such as hydrogen, and stored or used for reaction downstream with the ammonia produced to form urea.

It is desirable to remove water from the carbon dioxide-depleted synthesis gas. Water removal, or drying, is desirable to protect the downstream methanol synthesis catalyst, improve the kinetics of the methanol synthesis reaction and to minimise water in the crude methanol product. Water removal may also improve the performance and reliability of the first stage of compression. Water removal may be accomplished by cooling the water-containing gas below the dew point using one or more stages of heat exchange and passing the resulting stream through a gas liquid separator. Further stages of drying, e.g. with a desiccant may be performed if desired.

Methanol may be synthesised from the carbon dioxide-depleted synthesis gas. Any methanol production technology may be used. Methanol is synthesised in a methanol synthesis unit, which may comprise a methanol converter containing a methanol synthesis catalyst. The process can be on a once-through or a recycle basis in which unreacted product gas, after optional condensate removal, is mixed with make-up gas comprising hydrogen and carbon oxides in the desired ratio and returned to the methanol reactor. The methanol synthesis, because it is exothermic, may involve cooling by indirect heat exchange surfaces in contact with the reacting gas, or by subdividing the catalyst bed and cooling the gas between the beds by injection of cooler gas or by indirect heat exchange. The methanol may be recovered by condensation. The methanol synthesis also produces water, which may also be fed to the formaldehyde production unit. The synthesis gas composition preferably has $PH_2 > 2PCO + 3PCO_2$ such that there is excess hydrogen to react with the oxides of carbon. The stoichiometry number, R, as defined by $R=([H_2]-[CO_2])/([CO]+[CO_2])$, of the synthesis gas fed to the methanol synthesis catalyst, is preferably ≥3, more preferably ≥4, most preferably ≥5.

An unreacted gas stream may be recovered from the methanol synthesis unit as a methanol synthesis off-gas. A methanol synthesis off-gas may therefore comprises nitrogen, hydrogen and residual carbon monoxide.

A purge gas stream may be removed to prevent the undesirable build-up of inert/unreactive gases. If desired methanol may also be synthesised from this purge gas, or hydrogen recovered from it, for example to adjust the stoichiometry of the resulting gas or to generate power.

Any methanol synthesis catalyst may be used, but preferably it is based on a promoted or un-promoted copper/zinc oxide/alumina composition, for example those having a copper content in the range 50-70% wt. Promoters include oxides of Mg, Cr, Mn, V, Ti, Zr, Ta, Mo, W, Si and rare earths. In the catalyst, the zinc oxide content may be in the range 20-90% wt, and the one or more oxidic promoter compounds, if present, may be present in an amount in the range 0.01-10% wt. Magnesium compounds are preferred promoters and the catalyst preferably contains magnesium in an amount 1-5% wt, expressed as MgO. The synthesis gas may be passed over the catalyst at a temperature in the range 200-320° C., and at a pressure in the range 20-250 bar abs, preferably 20-120 bar abs, more preferably 30-120, bar abs and a space velocity in the range 500-20000 h$^{-1}$. When the aim of the process is not to maximise methanol production, the inlet temperature of the methanol synthesis stage may be lower, e.g. 200-270° C. thus extending the catalyst lifetime by reducing sintering of the active copper sites.

A single stage of methanol synthesis may be sufficient. Nevertheless, if desired, the methanol synthesis may be part of a multiple synthesis process where the product gas, with or without condensate removal, is fed to one or more further methanol synthesis reactors, which may contain the same or different methanol synthesis catalyst. Such methanol production apparatus and catalysts are commercially available.

Crude methanol recovered from a methanol synthesis unit is conventionally purified by multiple stages of distillation. When the recovered methanol is oxidised to make formaldehyde, it is possible to simplify the methanol purification process. Therefore crude methanol recovered from the methanol synthesis stage may be used directly in the formaldehyde production unit without further purification. If desired however, the crude methanol may be subjected one or more purification stages, including a single de-gassing stage, in a methanol purification unit prior to feeding it to the oxidation reactor. The de-gassing stage or any distillation stages may be provided by distillation columns heated using heat recovered from the oxidation reactor or elsewhere in the process. In particular, the degassing stage may be heated using steam generated by the oxidation stage. This simplification of the purification offers significant savings in capital and operating costs for the process.

Methanol is oxidised to formaldehyde in step (a). Any formaldehyde production technology may be used. The formaldehyde is synthesised in formaldehyde production unit, which may comprise an oxidation reactor containing an oxidation catalyst. The oxidation catalyst may be provided as a fixed bed or preferably, within externally cooled tubes disposed within the reactor. Air, or air enriched in oxygen and methanol may be passed to the reactor containing an oxidation catalyst in which the methanol is oxidised.

Production of formaldehyde from methanol and oxygen may be performed either in a silver- or a metal oxide catalysed process operated at methanol-rich and methanol-lean conditions, respectively. Hence the oxidation catalyst may be selected from either a silver catalyst or a metal oxide oxidation catalyst, preferably an oxidation catalyst comprising a mixture of iron and molybdenum oxides. Vanadium oxide catalysts may also be used. In the metal oxide process the principal reaction is the oxidation of the methanol to formaldehyde;

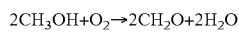

$$2CH_3OH+O_2 \rightarrow 2CH_2O+2H_2O$$

Over silver catalysts, in addition to the above oxidation reaction, methanol is also dehydrogenated in the principal reaction for this type of catalyst;

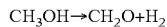

$$CH_3OH \rightarrow CH_2O+H_2$$

In the metal oxide process, formaldehyde is produced in multi-tube reactors. Typically, a reactor comprises 10-30,000 preferably 10-20,000 tubes filled up with ring-shaped or other shaped catalysts and cooled by oil or molten salts as heat transfer fluid. Since the reaction is highly exothermic ($\Delta H=-156$ kJ/mol), isothermal conditions are difficult to obtain and consequently a hotspot may be formed within the reaction zone. In order to limit the hot spot temperature, at the first part of the reactor the catalyst can be diluted with inert rings. The catalyst used in the oxide process is preferably a mixture of iron molybdate $Fe_2(MoO_4)_3$ and molybdenum trioxide $MoO_3$ with a molybdenum: iron atomic ratio between 2 and 3. In most aspects the catalytic performance is satisfactory; the plant yield is high (88-93 or 94%) and neither molybdenum nor iron are toxic, which is favourable considering both environmental and human health aspects.

Air is preferably used at levels to maintain the oxygen content at the inlet of the reactor below the explosive limit. The feed gas may therefore comprise ≤6.5% by volume methanol for a once-through reactor or about 8-11% by volume, preferably 8-9% by volume methanol where there is recirculation. The oxidation reactor may be operated adiabatically or isothermally, where the heat of reaction can be used to generate steam. The inlet to the oxidation reactor is typically in the range 80-270° C., preferably 150-270° C., with iron-based catalytic processes operating up to 400° C. and silver-based processes up to 650° C. The operating pressures are typically 1.1-5 bar abs, preferably 1.3-5 bar abs.

A single passage through the oxidation reactor can result in high yields of formaldehyde, or if desired it is possible to recycle unreacted gases, which comprise mainly nitrogen, from the vent gas separator to the reactor inlet to maintain a low oxygen concentration. Thus an oxygen-lean gas may be recovered from e.g. an absorber column and recycled to the feed stream to the reactor, e.g. to a feed line where the recycle gas is mixed with fresh air. A low oxygen concentration permits a higher methanol concentration at the reactor inlet. For example, if the oxygen content is about 11% vol, then the methanol concentration may be about 6.5% vol, but if the oxygen content is 13% vol or higher such concentrations are not suitable because the feed gas mixture is within the explosive limits.

Depending on the scale required in the present process, the stage may be operated with or without recycle of oxidised gas to the inlet of the oxidation reactor. Operation without recycle may be beneficial in smaller processes because this removes the need for a recycle compressor and hence offers further savings.

The formaldehyde—containing stream produced in the formaldehyde reactor is separated into a formaldehyde product stream and a vent gas. The separation unit may comprise absorption to extract the formaldehyde product from the oxidised gas mixture into either water to produce aqueous formaldehyde solution, or a urea solution to produce a urea-formaldehyde concentrate (UFC). The absorption may be performed using an absorption tower, which may contain a selection of packing, trays and other features to promote the absorption, and cooling water may be used to provide the product at a temperature in the range 20-100° C. The absorption stage typically runs at a slightly lower pressure than the reactor.

Urea formaldehyde concentrate that may be produced typically comprises a mixture of about 60% wt formaldehyde, about 25% wt urea and the balance about 15% wt water. Such a product may be termed "UFC85". Other UFC products may also be produced. Other formaldehyde products may also be produced. Excess formaldehyde products may be sold. The products made from the formaldehyde may be used to stabilise urea.

The formaldehyde production unit generates a vent gas. The vent gas may optionally be treated in a vent gas treatment unit such as an emission control system (ECS). An ECS may comprise a catalytic combustor that reacts any carbon monoxide, methanol, formaldehyde and dimethyl ether in the vent gas with oxygen. The gas emitted from an ECS, i.e. an ECS effluent, typically comprises carbon dioxide, steam and nitrogen and therefore may be recycled, preferably after suitable compression, to the process. Thus the ECS effluent may be passed to a carbon dioxide-removal stage of a synthesis gas generation unit where steam and carbon dioxide may be recovered, to provide additional nitrogen in the synthesis gas. Alternatively the ECS effluent may be provided to a methanol synthesis unit where the carbon dioxide may be reacted with hydrogen in the synthesis gas to produce additional methanol. Alternatively, the ECS effluent may be fed to the urea production unit to provide carbon dioxide for additional urea production. The ECS effluent may be provided to one or more of these alternatives.

In another embodiment, the vent gas treatment unit comprises a gas-liquid separator that separates the nitrogen-rich off-gas from liquid methanol, which may be recycled to the oxidation reactor directly or after one or more stages of purification. The nitrogen-rich gas separated in the separator may be compressed and passed to another process unit, such as an ammonia synthesis unit.

Alternatively the formaldehyde vent gas may be recycled directly to the process without treatment. In one embodiment, the formaldehyde vent gas is recycled directly to a synthesis gas generation unit as a fuel gas so that the organic contaminants present in the vent gas may be combusted to generate energy. The formaldehyde vent gas may, for example, be recycled directly to the fuel gas stream of a primary reformer or may be fed to a furnace for steam generation. In this way an ECS or vent gas treatment unit is not required, which offers considerable savings.

Alternatively, the formaldehyde vent gas may be recycled directly to a carbon dioxide removal stage so that the carbon dioxide and water vapour present in the vent gas may be captured. Organic contaminants such as methanol, formaldehyde and dimethyl ether may also be captured, e.g. using a PSA unit.

Alternatively, the formaldehyde vent gas may be recycled directly to a methanol synthesis stage. Direct recycling is simpler and is preferred. With direct recycling, the by-products will be limited by equilibrium across the methanol synthesis catalyst and so will not accumulate in this recycle loop. The nitrogen is also recovered without the need for catalytic combustion or intensive pressurisation.

The formaldehyde vent gas may be recycled directly to one or more of these alternatives.

An additional advantage of the present invention is that the absorber column used in formaldehyde product recovery may be significantly simplified. Such columns typically comprise multiple stages comprising trays and packing. An upper or second stage of the absorber is useful to provide flexibility in formaldehyde product recovery but adds to the complexity and cost of the absorber. Because the vent gas is recycled to the process, the present invention may permit both the omission of the vent gas treatment unit and the upper stage of the absorber, which may be replaced with a simpler condenser.

The formaldehyde production unit may also produce an aqueous waste stream, for example a condensate recovered as a by-product of the methanol oxidation. This condensate may contain organic compounds such as methanol, formaldehyde and dimethyl ether and therefore provides a potential source of hydrocarbon. In one embodiment, the process condensate is recycled to a synthesis gas generation stage where it is used to generate steam for use in steam reforming. The steam may be formed in a conventional boiler and added to the hydrocarbon feed or may, preferably, be generated in a saturator to which the aqueous effluent and hydrocarbon are fed.

One particular embodiment of the process of the invention comprises a process for the production of a formaldehyde-stabilised urea product comprising the steps of (a) generating a synthesis gas comprising hydrogen, nitrogen, carbon monoxide, carbon dioxide and steam in a synthesis gas generation unit; (b) recovering carbon dioxide from the synthesis gas to form a carbon dioxide-depleted synthesis gas; (c) synthesising methanol from the carbon dioxide-depleted synthesis gas in a methanol synthesis unit and recovering the methanol and a methanol synthesis off-gas comprising nitrogen, hydrogen and residual carbon monoxide; (d) subjecting at least a portion of the recovered methanol to oxidation with air in a formaldehyde production unit according to the invention; (e) subjecting the methanol synthesis off-gas to methanation in a methanation reactor containing a methanation catalyst to form an ammonia synthesis gas; (f) optionally synthesising ammonia from the ammonia synthesis gas in an ammonia production unit and recovering the ammonia; (g) reacting ammonia and at least a portion of the recovered carbon dioxide stream in a urea production unit to form a urea stream; and (h) stabilising the urea by mixing the urea stream and a stabiliser prepared using formaldehyde recovered from the formaldehyde production unit.

In the methanation stage (e), residual carbon monoxide and carbon dioxide in the methanol synthesis off-gas stream is converted to methane in the methanator. Any suitable arrangement for the methanator may be used. Thus the methanator may be operated adiabatically or isothermally. One or more methanators may be used. A nickel-based methanation catalyst may be used. For example, in a single methanation stage the gas from the methanol synthesis stage may be fed at an inlet temperature in the range 200-400° C. to a fixed bed of pelleted nickel-containing methanation catalyst. Such catalysts are typically pelleted compositions, comprising 20-40% wt nickel. Such methanation apparatus and catalysts are commercially available. The pressure for methanation may be in the range 10-80 bar abs or higher up to 250 bar abs. Steam is formed as a by-product of methanation. The steam is desirably removed using conventional means such as cooling and separation of condensate. An ammonia synthesis gas stream may be recovered from the methanation and drying stage. Such methanation apparatus and catalysts are commercially available.

The methanated gas stream may be fed to an ammonia production unit as the ammonia synthesis gas. However, the hydrogen: nitrogen molar ratio of the methanated gas stream may need to be adjusted, for example by addition of nitrogen from a suitable source, to provide the ammonia synthesis gas. The adjustment of the hydrogen: nitrogen molar ratio is to ensure the ammonia synthesis reaction operates efficiently. The nitrogen may be provided from any source, for example from an air separation unit (ASU). The adjustment may be performed by direct addition of nitrogen to the methanated gas stream. The adjusted gas mixture may then be passed to an ammonia synthesis unit as the ammonia synthesis gas.

Ammonia may be synthesised in step (f). If ammonia is not synthesised as part of the integrated process of the invention, then ammonia may be provided for urea synthesis separately. When an ammonia synthesis step is present, the ammonia synthesis gas may be compressed to the ammonia synthesis pressure and passed to an ammonia production unit. The ammonia production unit comprises an ammonia converter containing an ammonia synthesis catalyst. The nitrogen and hydrogen react together over the catalyst to form the ammonia product Ammonia synthesis catalysts are typically iron based but other ammonia synthesis catalysts may be used. The reactor may operate adiabatically or may be operated isothermally The catalyst beds may be axial and/or radial flow and one or more beds may be provided within a single converter vessel. The conversion over the catalyst is generally incomplete and so the synthesis gas is typically passed to a loop containing a partially reacted gas mixture recovered from the ammonia converter and the resulting mixture fed to the catalyst. The synthesis gas mixture fed to the loop may have a hydrogen: nitrogen ratio of 2.2-3.2. In the ammonia production unit, the hydrogen/nitrogen mixture may be passed over the ammonia synthesis catalyst at high pressure, e.g. in the range 80-350 bar abs, preferably 150-350 bar abs for large-scale plants, and a temperature in the range 300-540° C., preferably 350-520° C.

A purge gas stream containing methane and hydrogen may be taken from the ammonia synthesis loop and fed to the synthesis gas generation step or used as a fuel.

Compression of the synthesis gas is preferably effected in multiple stages, with a first and a second stage performed before the methanol synthesis to achieve e.g. 50-100 barg, preferably 80-100 barg, and a third stage after methanation to achieve a higher pressure, e.g. 150-250 barg, before the ammonia synthesis. Thus methanol synthesis may usefully be provided between the second and third stages of compression, with the methanator downstream of methanol synthesis and upstream of the third stage of compression. Alternatively, the methanol synthesis may usefully be provided upstream of the first stage of compression.

Urea may be produced in step (g) by reacting ammonia from step (f), or supplied as a separate feed, with carbon dioxide recovered from step (d). Typically only a portion of the ammonia produced in step (f) will be used to produce urea, which is limited by the amount of carbon dioxide recovered in step (b). Excess ammonia may be recovered and used to make nitric acid, ammonium nitrate or ammonia products for sale. Any urea production technology may be used. For example, ammonia and carbon dioxide may be combined in a first reactor at 140-200° C. and 120-220 bar abs to form ammonium carbamate as follows;

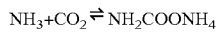

$$NH_3 + CO_2 \rightleftharpoons NH_2COONH_4$$

The ammonium carbamate is then dehydrated in a further reactor to form urea;

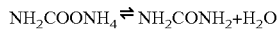

$$NH_2COONH_4 \rightleftharpoons NH_2CONH_2 + H_2O$$

The high pressure favours ammonium carbamate formation and the high temperature favours the dehydration, so the resultant mixture contains all the above components. Unreacted carbamate is therefore generally decomposed back to ammonia and carbon dioxide, which may then be recycled to the reactor. The carbon dioxide readily dissolves in the water from the dehydration, which if recycled supresses the equilibria and so the system may be run with excess ammonia to minimise this recycle. The decomposition and subsequent recycling can be carried out in one or more successive stages at decreasing pressures to minimise the ultimate concentration of ammonium carbamate dissolved in the urea solution. An alternative process arrangement uses the fresh carbon dioxide gas to strip unreacted ammonia and carbon dioxide from the ammonium carbamate and urea solution at the same pressure as the reactor. Further unreacted material is recycled from lower pressure stages as ammonium carbamate solution. Such urea production apparatus is commercially available.

Formaldehyde-stabilised urea is produced in step (h) by mixing urea produced in step (g) and a stabiliser prepared using formaldehyde recovered from the formaldehyde production unit in step (d). The stabiliser may be any formaldehyde-based stabiliser; including aqueous formaldehyde and an aqueous urea-formaldehyde concentrate. Aqueous formaldehyde and urea formaldehyde concentrate may be prepared directly in the formaldehyde production unit. Formaldehyde, either as a concentrated solution or as a combined solution of urea and formaldehyde may be added to molten urea prior to forming into either prills or granules. This reduces the tendency of the urea to absorb moisture and increases the hardness of the surface of the solid particles, preventing both caking (bonding of adjacent particles) and dusting (abrasion of adjacent particles). This maintains the free flowing nature of the product; prevents loss of material through dust, and enhances the stability during long term storage. If urea is available then it is preferable to use the urea formaldehyde solution as a stable solution with a higher formaldehyde concentration can be produced, which minimises the water being added to the molten urea. Such stabilised urea production apparatus is commercially available.

In FIG. 1, a natural gas stream 10, steam 16 and an air stream 12 are fed to a synthesis gas generation unit 18 comprising a primary reformer, a secondary reformer and a water-gas shift unit comprising high- and low-temperature shift converters. The natural gas is primary reformed with steam in externally-heated catalyst filled tubes and the primary reformed gas subjected to secondary reforming in the secondary reformer with air to generate a raw synthesis gas comprising nitrogen, hydrogen, carbon dioxide, carbon monoxide and steam. The steam to carbon monoxide ratio of the raw synthesis gas is adjusted by steam addition if necessary and the gas subjected to high temperature shift and low temperature shift in shift converters containing high and low temperature shift catalysts to generate a shifted synthesis gas mixture 22 in which the hydrogen and carbon dioxide contents are increased and the steam and carbon monoxide contents decreased. Steam 20, generated by cooling the secondary and shifted gas streams, may be exported from the synthesis gas generation unit 18. The shifted synthesis gas 22 is fed to a carbon dioxide removal unit 24 operating by means of reactive absorption. A carbon dioxide and water stream is recovered from the separation unit 24 by line 26 for further use. A carbon dioxide-depleted synthesis gas 28 comprising hydrogen, carbon monoxide and nitrogen is passed from the carbon dioxide removal unit 24 to a methanol synthesis unit 30 comprising a methanol converter containing a bed of methanol synthesis catalyst. If desired, upstream of the methanol synthesis unit 30, steam in the shifted gas may be removed by cooling and separation of condensate. Methanol is synthesised in the converter and separated from the product gas mixture and recovered from the methanol synthesis unit 30 by line 32 and passed to a formaldehyde production unit 34 comprising an oxidation reactor containing an oxidation catalyst. Air is fed via line 36 to the oxidation reactor where it is reacted with methanol from line 32 to produce formaldehyde. The formaldehyde production unit is fed with cooling water 38 and generates a steam stream 40 and a formaldehyde vent gas 42. Other feed streams to the formaldehyde production unit may include boiler feed water, process water and caustic (not shown). The formaldehyde is recovered in an absorption tower which may be fed with urea, e.g. from the urea synthesis unit 64, such that either aqueous formaldehyde or a urea-formaldehyde concentrate (UFC) product stream 44 may be recovered from the formaldehyde production unit 34 for further use. A methanol synthesis off-gas stream 46 comprising hydrogen, nitrogen and unreacted carbon monoxide recovered from the methanol synthesis unit 30 is passed to a methanation unit 48 comprising a methanation reactor containing a bed of methanation catalyst. Carbon oxides remaining in the off-gas 46 are converted to methane and water in the methanation reactor. Water is recovered from the methanation unit 48 by line 50. The methanated off-gas is an ammonia synthesis gas comprising essentially nitrogen and hydrogen and methane. The ammonia synthesis gas is passed from the methanation unit 48 by line 52 to an ammonia synthesis unit 54 comprising an ammonia converter containing one or more beds of ammonia synthesis catalyst Ammonia is produced in the converter and recovered from the ammonia synthesis unit 54 by line 56. A purge gas stream 60 comprising methane and unreacted hydrogen and nitrogen is recovered from the ammonia synthesis unit 54 and provided to the synthesis gas generation unit 18 as fuel and/or feed to the primary and/or secondary reformers. A vent gas stream 62 is also recovered from the ammonia synthesis unit 54. A portion 58 of the ammonia is separated from the product stream 56. The remaining ammonia is passed to a urea synthesis unit 64 where it is reacted with purified carbon dioxide provided by stream 26 to produce a urea stream and water. Water is recovered from the urea synthesis unit 64 by line 66. The urea stream is passed by line 68 to a stabilisation unit 70 comprising a stabilisation vessel where it is treated with aqueous formaldehyde or urea formaldehyde concentrate provided by line 44 to form a formaldehyde-stabilised urea product. The formaldehyde-stabilised urea product is recovered from the stabilisation unit 70 by line 72.

In this embodiment, the vent gas stream 42 from the formaldehyde production unit 34 is passed to an emission control system (ECS) 100 comprising a catalytic combustor in which the organic vent gas components are converted to carbon dioxide and steam. The combusted gas mixture, (i.e. ECS effluent) which comprises nitrogen, carbon dioxide and steam may be suitably compressed and recycled from the emission control system 100 to the process. In one embodiment, the combusted gas mixture from the ECS unit 100 is passed by line 102 to the methanol synthesis unit 30 where the carbon dioxide may be reacted with hydrogen in the synthesis gas to generate additional methanol. Alternatively or additionally, the combusted gas mixture may be provided by line 106 to the carbon dioxide removal unit 24 where the steam and carbon dioxide are removed to provide additional nitrogen in the synthesis gas. Alternatively or additionally, the combusted gas mixture may be provided via line 104 to the urea production unit 64 where the carbon dioxide is reacted to produce additional urea.

Figure 2:
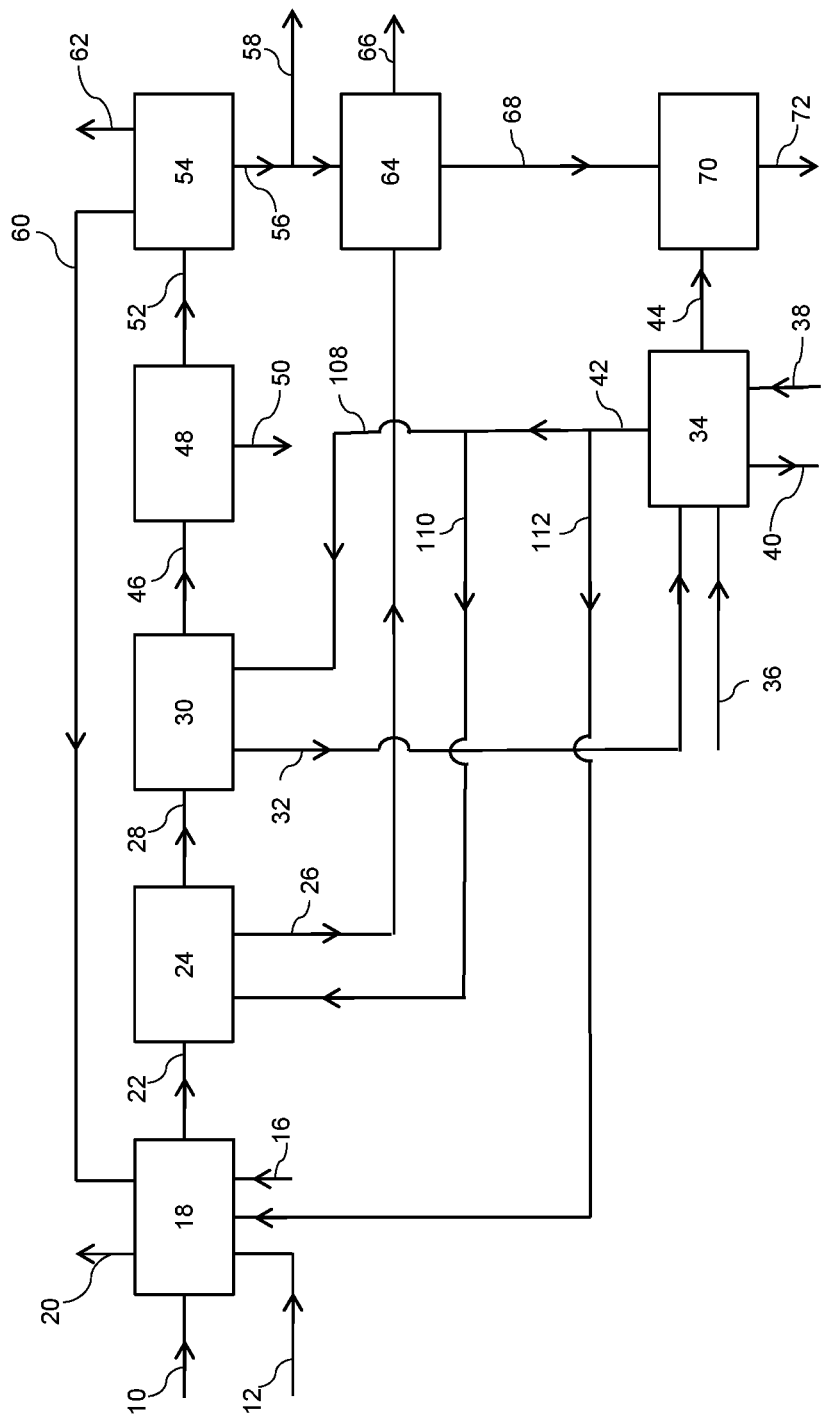
FIG. 2 is a schematic representation of a process according to a second aspect of the present invention.

In FIG. 2, the same synthesis gas generation, carbon dioxide removal, methanol synthesis, methanation, ammonia synthesis, urea synthesis and stabilisation units 18, 24, 30, 48, 54, 64 & 70 as set out in FIG. 1 are provided. In this embodiment, the vent gas stream 42 from the formaldehyde production unit 34 is recycled directly, without treatment in an ECS or other vent gas treatment units, to the process. In one embodiment, vent gas stream is passed by line 108 to the methanol synthesis unit 30 where the carbon dioxide is reacted with hydrogen to generate methanol. Alternatively or in addition, the vent gas stream may be passed by line 110 to the carbon dioxide removal unit 24 where the steam and carbon dioxide are removed. Alternatively or in addition, the vent gas stream may be passed by line 112 to the synthesis gas generation unit 18 as a fuel.

What is claimed is:

1. A process for producing formaldehyde, comprising:
   (a) oxidizing methanol with air in a formaldehyde production unit, thereby producing a formaldehyde-containing stream; and
   (b) separating said formaldehyde-containing stream in a separation unit into a formaldehyde product stream and a formaldehyde vent gas stream; wherein the formaldehyde vent gas stream, after treatment in a vent gas treatment unit, is passed to one or more stages of: (i) a synthesis gas generation unit, (ii) a carbon dioxide removal unit, (iii) a methanol synthesis unit or (iv) a urea synthesis unit; wherein
   the vent gas treatment unit comprises an emission control system comprising a catalytic combustor to convert the vent gas stream into carbon dioxide, nitrogen, and steam.

2. The process of claim 1, wherein the formaldehyde production unit comprises an oxidation reactor containing a bed of oxidation catalyst, the process further comprising recycling a portion of the formaldehyde vent gas stream to the oxidation reactor.

3. The process of claim 1, comprising recycling the formaldehyde vent gas to the methanol synthesis unit.

4. The process of claim 1, comprising passing the formaldehyde vent gas to the carbon dioxide removal unit; wherein the carbon dioxide removal unit is a unit for removing carbon dioxide from a synthesis gas generated in the synthesis gas generation unit.

5. The process of claim 1, comprising passing the formaldehyde vent gas to the urea synthesis unit.

6. The process of claim 1, comprising passing the formaldehyde vent gas to the synthesis gas generation unit, wherein the formaldehyde vent gas is used in the synthesis gas generation unit as a component of a fuel gas.

7. The process of claim 1, comprising passing the formaldehyde vent gas to the synthesis gas generation unit, wherein the formaldehyde vent gas stream is used in the synthesis gas generation unit as a feedstock.

8. The process of claim 1, wherein the formaldehyde production unit comprises an oxidation reactor containing a bed of oxidation catalyst, wherein the process is operated without recycling any of the formaldehyde vent gas stream to the oxidation reactor.

9. A process for producing formaldehyde, comprising (a) oxidizing methanol with air in a formaldehyde production unit, thereby producing a formaldehyde-containing stream; and (b) separating said formaldehyde-containing stream into a formaldehyde product stream and a formaldehyde vent gas stream; wherein the formaldehyde vent gas stream, optionally after treatment in a vent gas treatment unit, is passed to one or more stages of: (i) a methanol synthesis unit or (ii) a urea synthesis unit.

10. A process for producing formaldehyde, comprising (a) oxidizing methanol with air in a formaldehyde production unit, thereby producing a formaldehyde-containing stream; and (b) separating said formaldehyde-containing stream into a formaldehyde product stream and a formaldehyde vent gas stream; wherein the formaldehyde vent gas stream, without treatment in a vent gas treatment unit, is passed to one or more stages of a carbon dioxide removal unit operating by either reactive absorption, physical absorption, or pressure-wing adsorption.

* * * * *